United States Patent
Xiao et al.

(10) Patent No.: US 11,318,296 B2
(45) Date of Patent: May 3, 2022

(54) SIGNAL-BASED AUTOMATED DEEP BRAIN STIMULATION PROGRAMMING

(71) Applicant: Medtronic, Inc., Minneapolis, MN (US)

(72) Inventors: Yizi Xiao, Eden Prairie, MN (US); Eric J. Panken, Edina, MN (US); Scott R. Stanslaski, Shoreview, MN (US); Jadin C. Jackson, Roseville, MN (US); Christopher Pulliam, Plymouth, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 739 days.

(21) Appl. No.: 16/172,435

(22) Filed: Oct. 26, 2018

(65) Prior Publication Data
US 2020/0129757 A1    Apr. 30, 2020

(51) Int. Cl.
*A61N 1/05* (2006.01)
*A61N 1/36* (2006.01)
*A61N 1/372* (2006.01)

(52) U.S. Cl.
CPC ......... *A61N 1/0534* (2013.01); *A61N 1/3616* (2013.01); *A61N 1/36139* (2013.01); *A61N 1/37247* (2013.01)

(58) Field of Classification Search
CPC ............................ A61N 1/0534; A61N 1/36139
USPC ............................................................. 607/2
See application file for complete search history.

(56) References Cited

U.S. PATENT DOCUMENTS

| | | |
|---|---|---|
| 8,280,514 B2 | 10/2012 | Lozano et al. |
| 8,615,299 B2 | 12/2013 | Goetz |
| 8,700,150 B2 | 4/2014 | Libbus et al. |
| 9,119,543 B2 | 9/2015 | Martens |
| 10,095,837 B2 | 10/2018 | Corey et al. |
| 2003/0236487 A1 | 12/2003 | Knowlton |
| 2009/0099627 A1 | 4/2009 | Molnar et al. |
| 2011/0264165 A1 | 10/2011 | Molnar et al. |
| 2012/0150256 A1 | 6/2012 | Martens |
| 2014/0074187 A1 | 3/2014 | Molnar |
| 2016/0296759 A1 | 10/2016 | Cong et al. |
| 2017/0259064 A1* | 9/2017 | Wu ................... A61N 1/36185 |

FOREIGN PATENT DOCUMENTS

| | | |
|---|---|---|
| WO | 2016/030424 A1 | 3/2016 |
| WO | 2018080653 A1 | 5/2018 |

OTHER PUBLICATIONS

U.S. Appl. No. 16/395,320, filed Apr. 26, 2019, by Jackson et al.

(Continued)

*Primary Examiner* — Nadia A Mahmood
(74) *Attorney, Agent, or Firm* — Shumaker & Sieffert, P.A.

(57) ABSTRACT

Techniques are disclosed to automate determination of therapy parameter values for adaptive deep brain stimulation (aDBS). A medical device may determine differences in power values between a present and a previous power value. Based on the difference being greater than or equal to a threshold value, the medical device may iteratively adjust a present therapy parameter value until the difference in the power values between a present and a previous power value is less than the threshold value.

24 Claims, 5 Drawing Sheets

(56) References Cited

OTHER PUBLICATIONS

Tinkhauser et al., "Directional Local Field Potentials: A Tool to Optimize Deep Brain Stimulation," Movement Disorders, Nov. 2017, 6 pp.

De Solages et al., "Maximal Subthalamic Beta Hypersynchrony of the Local Field Potential in Parkinson's Disease is Located in the Central Region of the Nucleus," Journal of Neurology, Neurosurgery, and Psychiatry, vol. 82, Jan. 4, 2011, pp. 1387-1389.

Gunalan et al., "Creating and Parameterizing Patient-Specific Deep Brain Stimulation Pathway-Activation Models Using the Hyperdirect Pathway as an Example," PLoS ONE, vol. 12, No. 4, Apr. 25, 2017, 19 pp.

Horn et al., "Toward an Electrophysiological "Sweet Spot" for Deep Brain Stimulation in the Subthalamic Nucleus," Human Brain Mapping, Mar. 2017, 14 pp.

Zaidel et al., "Subthalamic Span of B Oscillations Predicts Deep Brain Stimulation Efficacy for Patients with Parkinson's Disease," Brain, vol. 133, Jun. 9, 2010, pp. 2007-2021.

\* cited by examiner

SIGNAL-BASED AUTOMATED DEEP BRAIN STIMULATION PROGRAMMING

TECHNICAL FIELD

This disclosure generally relates to electrical stimulation therapy.

BACKGROUND

Medical devices may be external or implanted, and may be used to deliver electrical stimulation therapy to various tissue sites of a patient to treat a variety of symptoms or conditions such as chronic pain, tremor, Parkinson's disease, other movement disorders, epilepsy, urinary or fecal incontinence, sexual dysfunction, obesity, or gastroparesis. A medical device delivers electrical stimulation therapy via one or more leads that include electrodes located proximate to target locations associated with the brain, the spinal cord, pelvic nerves, peripheral nerves, or the gastrointestinal tract of a patent. For bipolar stimulation, the electrodes used for stimulation may be on one or more leads. For unipolar stimulation, the electrodes may be on one or more leads, and an electrode on a stimulator housing located remotely from the target site (e.g., near clavicle). It may be possible to use leadless stimulation using electrodes mounted on the stimulation housing. Hence, electrical stimulation is used in different therapeutic applications, such as adaptive deep brain stimulation (aDBS), spinal cord stimulation (SCS), pelvic stimulation, gastric stimulation, or peripheral nerve field stimulation (PNFS).

A clinician may select values for a number of programmable parameters in order to define the electrical stimulation therapy to be delivered by the implantable stimulator to a patient. For example, the clinician may select one or more electrodes for delivery of the stimulation, a polarity of each selected electrode, a voltage or current pulse amplitude, a pulse width, and a pulse frequency as stimulation parameters. A set of parameters, such as a set including electrode combination, electrode polarity, amplitude, pulse width, and pulse rate, may be refereed to as a program in the sense that they define the electrical stimulation therapy to be delivered to the patient.

SUMMARY

This disclosure describes example techniques to titrate a therapy parameter, for automated stimulation programming, such that delivery of the electrical stimulation based on the therapy parameter compensates for effects from a signal source within a patient. In adaptive deep brain stimulation (aDBS), a medical device (e.g., implantable medical device (IMD) or programmer) may determine which electrodes are most proximate to a signal source within the patient. The electrodes that are most proximate to the signal source tend to be the electrodes that should be used to deliver therapy, e.g., in terms of efficacy of the therapy in alleviating a condition associated with the signal source. This disclosure describes example techniques for determining therapy parameters for therapy delivery with the electrodes that are proximal to the signal source. For example, the medical device may determine a difference between a power of a frequency band relative to a previous power of the frequency band (e.g., in response to delivery of a previous electrical stimulation), and determine whether the difference is less than or greater than a difference threshold value. The medical device may keep adjusting a therapy parameter value until the difference in the power of the frequency band relative to the previous power of the frequency band is less than the difference threshold value. The final therapy parameter value may be the parameter value that results in the difference being less than the difference threshold value. The IMD may then deliver therapy based on the final therapy parameter value. In some examples, physician or clinician confirmation of the final therapy parameter value may be needed before the IMD delivers therapy based on the final therapy parameter value.

In this manner, the example techniques may provide a relatively fast way in which to determine the therapy parameter value to provide a technical solution to a technical problem of determining the appropriate therapy parameter values. For instance, rather than manual entry of different therapy parameters and receiving patient feedback for the efficacy, the medical device may automate the process of determining the therapy parameter values based on whether differences in a current power and a previous power of a frequency band are greater than or less than a difference threshold value.

In one example, this disclosure describes a method comprising determining, with processing circuitry, a present power value of power in a frequency band in a bioelectric signal, generated in a brain, in response to delivery of present electrical stimulation having a present therapy parameter value, determining, with the processing circuitry, a power band difference value between the present power value and a previous power value, wherein the previous power value is indicative of power in the frequency band in a previous bioelectric signal, generated in the brain, in response to delivery of a previous electrical stimulation having a previous therapy parameter value different than the present therapy parameter value, comparing, with the processing circuitry, the power band difference value to a threshold value, based on the power band difference value being greater than or equal to the threshold value, iteratively setting, with the processing circuitry, the previous therapy parameter value equal to the present therapy parameter value and adjusting, with the processing circuitry, the present therapy parameter value until the power band difference value is less than the threshold value, setting, with the processing circuitry, a final therapy parameter value based on the present therapy parameter value, and causing, with the processing circuitry, delivery of electrical stimulation having the final therapy parameter value.

In one example, this disclosure describes a system comprising a medical device comprising a memory and processing circuitry. The processing circuitry is configured to determine a present power value of power in a frequency band in a bioelectric signal, generated in a brain, in response to delivery of present electrical stimulation having a present therapy parameter value, determine a power band difference value between the present power value and a previous power value, wherein the previous power value is indicative of the power in the frequency band in a previous bioelectric signal, generated in the brain, in response to delivery of a previous electrical stimulation having a previous therapy parameter value different than the present therapy parameter value, and wherein the previous power value is stored in the memory, compare the power band difference value to a threshold value, based on the power band difference value being greater than or equal to the threshold value, iteratively set the previous therapy parameter value equal to the present therapy parameter value and adjust the present therapy parameter value until the power band difference value is less than the threshold value, set a final therapy parameter value based on the present therapy parameter value, and cause delivery of electrical stimulation having the final therapy parameter value.

In one example, this disclosure describes a computer-readable storage medium storing instructions that when executed cause one or more processors of a medical device to determine a present power value of power in a frequency band in a bioelectric signal, generated in a brain, in response to delivery of present electrical stimulation having a present therapy parameter value, determine a power band difference value between the present power value and a previous power value, wherein the previous power value is indicative of power in the frequency band in a previous bioelectric signal, generated in the brain, in response to delivery of a previous electrical stimulation having a previous therapy parameter value different than the present therapy parameter value, compare the power band difference value to a threshold value, based on the power band difference value being greater than or equal to the threshold value, iteratively set the previous therapy parameter value equal to the present therapy parameter value and adjust the present therapy parameter value until the power band difference value is less than the threshold value, set a final therapy parameter value based on the present therapy parameter value, and cause delivery of electrical stimulation having the final therapy parameter value.

The details of one or more examples of the techniques of this disclosure are set forth in the accompanying drawings and the description below. Other features, objects, and advantages of the techniques will be apparent from the description and drawings, and from the claims.

DETAILED DESCRIPTION

This disclosure describes example techniques to automatically determine values of electrical stimulation therapy parameters, such as electrical stimulation amplitude values, for therapy after determining which electrodes to use for therapy. In some examples, an implantable medical device (IMD) determines orientation of a signal source within the brain, relative to the lead, and determines electrodes on a lead that are most proximal to the signal source. As described in more detail, as one non-limiting example way to determine the electrodes on the lead that are most proximal are the electrodes, is to determine the electrodes having the highest current source density (CSD). The electrodes determined to be most proximal to the signal source are electrodes that are selected to deliver therapy. However, once the orientation of the signal source, and which electrodes are most proximal to the signal source, are known, the clinician may need to expend a lengthy trial and error process to find the appropriate values for therapy parameters, such as amplitude, of the therapy to be delivered via the most proximal electrodes.

This disclosure describes example techniques that combine techniques for determining which electrode to use to deliver therapy once signal orientation is found with techniques for automatically determining therapy parameters. For instance, in step one, a medical device (e.g., the IMD or a programmer) determines source orientation and selects which electrodes are to be used to deliver therapy based on that determination. In step two, the medical device deploys an adaptive stimulation protocol on the selected electrodes to titrate one or more parameters of the stimulation for suppression of beta band signal power in the brain.

The IMD or programmer may titrate one or more of the therapy parameters using various example techniques. As one example, the amplitude of the stimulation therapy is gradually adjusted (e.g., increased) until a difference in a current beta band signal power a previous beta band signal power, e.g., obtained from local field potential (LFP) signals, is less than a predetermined threshold difference value, or until the patient experiences undesirable side effects. The IMD or programmer may set the amplitude value of the stimulation therapy equal to the current amplitude value that resulted in the current beta band signal power. In one example, to gradually adjust the amplitude, the IMD or programmer may adjust the amplitude in accordance with a binary search algorithm, as described in more detail. However, other algorithms can be used in addition to or instead of the binary search algorithm.

Figure 1:
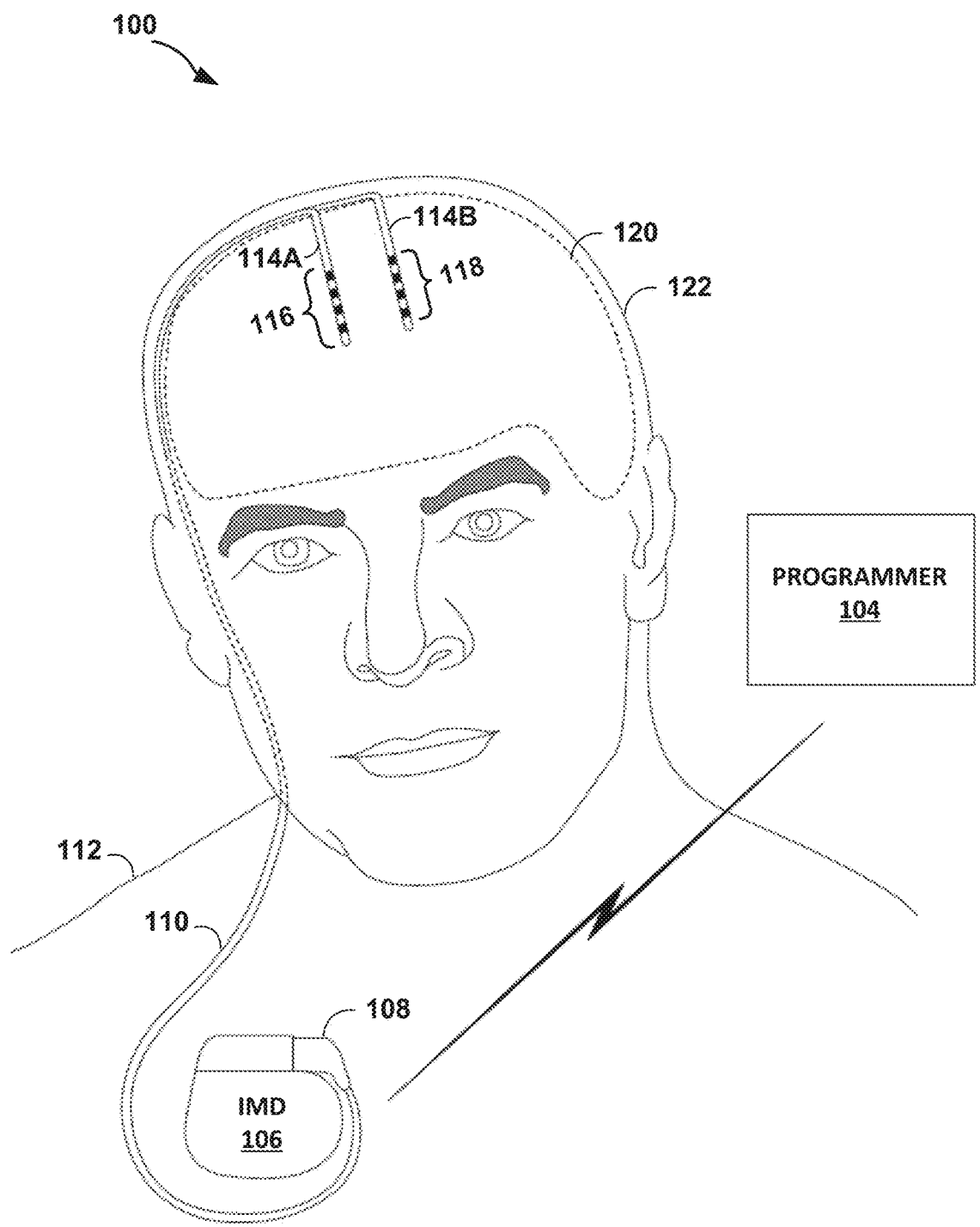
FIG. 1 is a conceptual diagram illustrating an example system that includes an implantable medical device (IMD) configured to deliver adaptive DBS to a patient according to an example of the techniques of the disclosure.

FIG. 1 is a conceptual diagram illustrating an example system 100 that includes an implantable medical device (IMD) 106 configured to deliver adaptive deep brain stimulation to a patient 112. DBS may be adaptive in the sense that IMD 106 may adjust, increase, or decrease the magnitude of one or more parameters of the DB S in response to changes in patient activity or movement, a severity of one or more symptoms of a disease of the patient, a presence of one or more side effects due to the DBS, or one or more sensed signals of the patient.

For instance, one example of system 100 is a bi-directional DBS system with capabilities to both deliver stimulation and sense intrinsic neuronal signals. System 100 provides for "closed-loop" therapy where IMD 106 may continuously monitor the state of certain biomarker signals and deliver stimulation according to pre-programmed routines based on the biomarker signals.

System 100 may be configured to treat a patient condition, such as a movement disorder, neurodegenerative impairment, a mood disorder, or a seizure disorder of patient 112. Patient 112 ordinarily is a human patient. In some cases, however, therapy system 100 may be applied to other mammalian or non-mammalian, non-human patients. While movement disorders and neurodegenerative impairment are primarily referred to herein, in other examples, therapy system 100 may provide therapy to manage symptoms of other patient conditions, such as, but not limited to, seizure disorders (e.g., epilepsy) or mood (or psychological) disorders (e.g., major depressive disorder (MDD), bipolar disorder, anxiety disorders, post-traumatic stress disorder, dysthymic disorder, and obsessive-compulsive disorder (OCD)). At least some of these disorders may be manifested in one or more patient movement behaviors. As described herein, a movement disorder or other neurodegenerative impairment may include symptoms such as, for example, muscle control impairment, motion impairment or other movement problems, such as rigidity, spasticity, bradykinesia, rhythmic hyperkinesia, nonrhythmic hyperkinesia, and akinesia. In some cases, the movement disorder may be a symptom of Parkinson's disease. However, the movement disorder may be attributable to other patient conditions.

Example therapy system 100 includes medical device programmer 104, implantable medical device (IMD) 106, lead extension 110, and leads 114A and 114B with respective sets of electrodes 116, 118. In the example shown in FIG. 1, electrodes 116, 118 of leads 114A, 114B are positioned to deliver electrical stimulation to a tissue site within brain 120, such as a deep brain site under the dura mater of brain 120 of patient 112. In some examples, delivery of stimulation to one or more regions of brain 120, such as the subthalamic nucleus, globus pallidus or thalamus, may be an effective treatment to manage movement disorders, such as Parkinson's disease. Some or all of electrodes 116, 118 also may be positioned to sense neurological brain signals within brain 120 of patient 112. In some examples, some of electrodes 116, 118 may be configured to sense neurological brain signals and others of electrodes 116, 118 may be configured to deliver adaptive electrical stimulation to brain 120. In other examples, all of electrodes 116, 118 are configured to both sense neurological brain signals and deliver adaptive electrical stimulation to brain 120. In some examples, unipolar stimulation may be possible where one electrode is on the housing of IMD 106.

IMD 106 includes a therapy module (e.g., which may include processing circuitry, signal generation circuitry or other electrical circuitry configured to perform the functions attributed to IMD 106) that includes a stimulation generator configured to generate and deliver electrical stimulation therapy to patient 112 via a subset of electrodes 116, 118 of leads 114A and 114B, respectively. The subset of electrodes 116, 118 that are used to deliver electrical stimulation to patient 112, and, in some cases, the polarity of the subset of electrodes 116, 118, may be referred to as a stimulation electrode combination. As described in further detail below, the stimulation electrode combination can be selected for a particular patient 112 and target tissue site (e.g., selected based on the patient condition). The group of electrodes 116, 118 includes at least one electrode and can include a plurality of electrodes. In some examples, the plurality of electrodes 116 and/or 118 may have a complex electrode geometry such that two or more electrodes are located at different positions around the perimeter of the respective lead.

In some examples, the neurological signals sensed within brain 120 may reflect changes in electrical current produced by the sum of electrical potential differences across brain tissue. Examples of neurological brain signals include, but are not limited to, bioelectric signals generated from local field potentials (LFP) sensed within one or more regions of brain 120. Electroencephalogram (EEG) signal or an electrocorticogram (ECoG) signal are also examples of bioelectric signals. For example, neurons generate the bioelectric signals, and if measured at depth, it is LFP, if measured on the dura, it is ECoG, and if on scalp, it is EEG.

One example of the feature of interest (e.g., biomarker) within the LFPs is synchronized beta frequency band (13-33 Hz) LFP activity recorded within the sensorimotor region of the subthalamic nucleus (STN) in Parkinson's disease patients. The source of the LFP activity can be considered as a signal source, within the brain of the patient, that outputs an oscillatory electrical voltage signal that is sensed by one or more of electrodes 116 and/or 118. The suppression of pathological beta activity (e.g., suppression or squelching of the signal component of the bioelectric signals generated from the LFP source that is within the beta frequency band) by both medication and DBS may correlate with improvements in the motor symptoms of patients who have Parkinson's disease.

In some examples, the neurological brain signals that are used to select a stimulation electrode combination may be sensed within the same region of brain 120 as the target tissue site for the electrical stimulation. As previously indicated, these tissue sites may include tissue sites within anatomical structures such as the thalamus, subthalamic nucleus or globus pallidus of brain 120, as well as other target tissue sites. The specific target tissue sites and/or regions within brain 120 may be selected based on the patient condition. Thus, in some examples, both a stimulation electrode combination and sense electrode combinations may be selected from the same set of electrodes 116, 118. In other examples, the electrodes used for delivering electrical stimulation may be different than the electrodes used for sensing neurological brain signals.

Electrical stimulation generated by IMD 106 may be configured to manage a variety of disorders and conditions. In some examples, the stimulation generator of IMD 106 is configured to generate and deliver electrical stimulation pulses to patient 112 via electrodes of a selected stimulation electrode combination. However, in other examples, the stimulation generator of IMD 106 may be configured to generate and deliver a continuous wave signal, e.g., a sine wave or triangle wave. In either case, a stimulation generator within IMD 106 may generate the electrical stimulation therapy for DBS according to a selected therapy program. In examples in which IMD 106 delivers electrical stimulation in the form of stimulation pulses, a therapy program may include a set of therapy parameter values (e.g., stimulation parameters), such as a stimulation electrode combination for delivering stimulation to patient 112, pulse frequency, pulse width, and a current or voltage amplitude of the pulses. As previously indicated, the electrode combination may indicate the specific electrodes 116, 118 that are selected to deliver stimulation signals to tissue of patient 112 and the respective polarities of the selected electrodes.

Figure 4A:
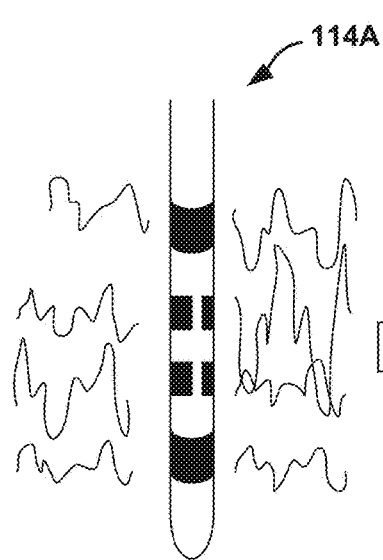
FIGS. 4A-4C are conceptual diagrams illustrating an example operation for determining therapy parameter value in accordance with an example of the techniques of this disclosure.
Figure 4B:
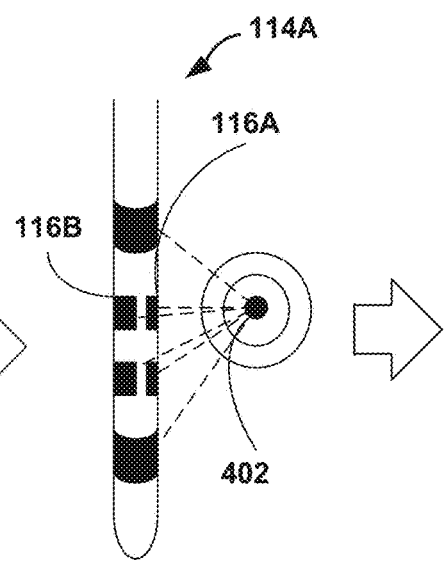
Figure 4C:
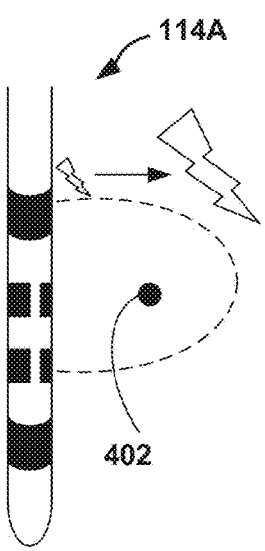

In some examples, electrodes 116, 118 may be radially-segmented DBS arrays (rDBSA) of electrodes. Radially-segmented DBS arrays refer to electrodes that are segmented radially along the lead. As one example, leads 114A and 114B may include a first set of electrodes arranged circumferentially around leads 114A and 114B that are all at the same height level on leads 114A and 114B. Each of the electrodes in the first set of electrodes is a separate segmented electrode and form a level of radially-segmented array of electrodes. Leads 114A and 114B may include a second set of electrodes arranged circumferentially around leads 114A and 114B that are all at the same height level on leads 114A and 114B. Each of the electrodes in the first set of electrodes is a separate segmented electrode and form a level of radially-segmented array of electrodes. The rDBSA electrodes may be beneficial for directional stimulation and sensing. An example of such electrodes is illustrated in FIGS. 4A-4C.

With rDBSA of electrodes, IMD 106 may be configured to perform both directional stimulation and sensing, thereby enhancing the ability to target the source of the LFP activities (also referred to as pathological neuronal activities). For example, with rDBSA, IMD 106 may be configured to perform directional sensing to determine a direction and/or orientation of the LFP source that generates the bioelectric signal having the signal component in the beta frequency band. Techniques to determine the direction and/or orientation of the LFP source are described in more detail below. Based on the determined direction and/or orientation, IMD 106 may direct the electrical stimulation toward the LFP source to suppress (e.g., squelch) the signal component produced by the source in the beta frequency band, as one example.

The signal component in the beta frequency band is described as one example, and the techniques are applicable to other types of LFP activity. Furthermore, the example techniques are not limited to examples where electrodes 116, 118 are an rDBSA of electrodes. The example of using rDBSA of electrodes is described as a way of directional stimulation and sensing. However, the example techniques are also useable in examples where directional stimulation and sensing are not available or are not used. Moreover, there may be other ways of performing directional stimulation and sensing that do not require the use of an rDBSA of electrodes.

To suppress the signal component having the beta frequency band from the LFP source, IMD 106 may output an electrical stimulation signal that alters the way in which neurons of the LFP source produce signals. For example, the electrical stimulation either directly inhibits a certain neuronal population that includes the LFP source or excites one group of neurons which in turn suppresses another group of neurons (e.g., network effect). The stimulation may act on the neurons directly, and not necessarily on the signals the neurons (e.g., LFP source) produces.

As described in more detail, algorithms may be used to determine orientation of the LFP source relative to leads 114A and 114B, and the most proximal electrodes of electrodes 116 and 118 to the LFP source. In general, the electrodes of electrodes 116 and 118 that are most proximal to the LFP source tend to be the electrodes with which electrical stimulation should be delivered. Electrodes of electrodes 116 and 118 that are most proximal to the LFP source may be the electrodes having the highest current source density (CSD). For instance, electrodes of electrodes 116 and 118 that have the highest CSD are also the closest to the LFP source.

However, once the electrodes of electrodes 116 and 118 that should be used to deliver therapy are determined, a clinician may need to perform extensive trial and error process to determine the correct amplitude or other therapy parameters. As described in more detail, this disclosure describes example techniques to combine the source direction and/or orientation algorithm (e.g., algorithm to determine the direction and/or orientation of the LFP source) with adaptive stimulation to automatically select the optimal electrode combination and titrate the stimulation amplitude of the stimulation delivered via the electrode combination.

In this way, a clinician may not need to determine electrode configuration as well as amplitude through a lengthy trial and error process known as monopolar review. Moreover, even if the electrode configuration (e.g., which ones of electrodes 116 and 118 to use) is known based on the determination of the direction and/or orientation of the LFP source, the clinician may need to go through a trial and error process to determine the correct stimulation amplitude. With the example techniques, a medical device (e.g., IMD 106 or possibly programmer 104) may automate the determination of which electrodes to use and one or more therapy parameters (e.g., amplitude) of the electrical stimulation. Although the above example is described with respect to amplitude, the example techniques may be extended to other therapy parameters such as frequency and pulse width of the electrical stimulation.

IMD 106 may be implanted within a subcutaneous pocket above the clavicle, or, alternatively, on or within cranium 122 or at any other suitable site within patient 112. Generally, IMD 106 is constructed of a biocompatible material that resists corrosion and degradation from bodily fluids. IMD 106 may comprise a hermetic housing to substantially enclose components, such as a processor, therapy module, and memory.

As shown in FIG. 1, implanted lead extension 110 is coupled to IMD 106 via connector 108 (also referred to as a connector block or a header of IMD 106). In the example of FIG. 1, lead extension 110 traverses from the implant site of IMD 106 and along the neck of patient 112 to cranium 122 of patient 112 to access brain 120. In the example shown in FIG. 1, leads 114A and 114B (collectively "leads 114") are implanted within the right and left hemispheres (or in just one hemisphere in some examples), respectively, of patient 112 in order to deliver electrical stimulation to one or more regions of brain 120, which may be selected based on the patient condition or disorder controlled by therapy system 100. The specific target tissue site and the stimulation electrodes used to deliver stimulation to the target tissue site, however, may be selected, e.g., according to the identified patient behaviors and/or other sensed patient parameters. For example, the target tissue site may be the location of the LFP source that generates the bioelectric signal having a signal component in the beta frequency band. The stimulation electrodes used to deliver stimulation to the target tissue site may be those that are most proximal to the LFP source, e.g., as determined by the electrodes having the highest CSD. Other lead 114 and IMD 106 implant sites are contemplated. For example, IMD 106 may be implanted on or within cranium 122, in some examples. Leads 114A and 114B may be implanted within the same hemisphere or IMD 106 may be coupled to a single lead implanted in a single hemisphere, in some examples.

Existing lead sets include axial leads carrying ring electrodes disposed at different axial positions and so-called "paddle" leads carrying planar arrays of electrodes. Selection of electrode combinations within an axial lead, a paddle lead, or among two or more different leads presents a challenge to the clinician. In some examples, more complex lead array geometries may be used.

Although leads 114 are shown in FIG. 1 as being coupled to a common lead extension 110, in other examples, leads 114 may be coupled to IMD 106 via separate lead extensions or directly to connector 108. Leads 114 may be positioned to deliver electrical stimulation to one or more target tissue sites within brain 120 to manage patient symptoms associated with a movement disorder of patient 112. Leads 114 may be implanted to position electrodes 116, 118 at desired locations of brain 120 through respective holes in cranium 122. Leads 114 may be placed at any location within brain 120 such that electrodes 116, 118 are capable of providing electrical stimulation to target tissue sites within brain 120 during treatment. For example, electrodes 116, 118 may be surgically implanted under the dura mater of brain 120 or within the cerebral cortex of brain 120 via a burr hole in cranium 122 of patient 112, and electrically coupled to IMD 106 via one or more leads 114.

In the example shown in FIG. 1, electrodes 116, 118 of leads 114 are shown as ring electrodes. Ring electrodes may be used in DBS applications because ring electrodes are relatively simple to program and are capable of delivering an electrical field to any tissue adjacent to electrodes 116, 118. In other examples, electrodes 116, 118 may have different configurations. For example, at least some of the electrodes 116, 118 of leads 114 may have a complex electrode array geometry that is capable of producing shaped electrical fields. The complex electrode array geometry may include multiple electrodes (e.g., partial ring or segmented electrodes) around the outer perimeter of each lead 114, rather than one ring electrode. In this manner, electrical stimulation may be directed in a specific direction from leads 114 to enhance therapy efficacy and reduce possible adverse side effects from stimulating a large volume of tissue. For example, electrodes 116, 118 may be radially-segmented DBS arrays (rDBSA) of electrodes, as described above, and as illustrated in FIGS. 4A-4C.

In some examples, a housing of IMD 106 may include one or more stimulation and/or sensing electrodes. In some examples, leads 114 may have shapes other than elongated cylinders as shown in FIG. 1. For example, leads 114 may be paddle leads, spherical leads, bendable leads, or any other type of shape effective in treating patient 112 and/or minimizing invasiveness of leads 114.

IMD 106 includes a memory to store a plurality of therapy programs that each define a set of therapy parameter values. In some examples, IMD 106 may select a therapy program from the memory based on various parameters, such as sensed patient parameters and the identified patient behaviors. IMD 106 may generate electrical stimulation based on the parameters of the selected therapy program to manage the patient symptoms associated with a movement disorder.

External programmer 104 wirelessly communicates with IMD 106 as needed to provide or retrieve therapy information. Programmer 104 is an external computing device that the user, e.g., a clinician and/or patient 112, may use to communicate with IMD 106. For example, programmer 104 may be a clinician programmer that the clinician uses to communicate with IMD 106 and program one or more therapy programs for IMD 106. Alternatively, programmer 104 may be a patient programmer that allows patient 112 to select programs and/or view and modify therapy parameters. The clinician programmer may include more programming features than the patient programmer. In other words, more complex or sensitive tasks may only be allowed by the clinician programmer to prevent an untrained patient from making undesirable changes to IMD 106.

When programmer 104 is configured for use by the clinician, programmer 104 may be used to transmit initial programming information to IMD 106. This initial information may include hardware information, such as the type of leads 114 and the electrode arrangement, the position of leads 114 within brain 120, the configuration of electrode array 116, 118, initial programs defining therapy parameter values, and any other information the clinician desires to program into IMD 106. Programmer 104 may also be capable of completing functional tests (e.g., measuring the impedance of electrodes 116, 118 of leads 114).

The clinician may also store therapy programs within IMD 106 with the aid of programmer 104. During a programming session, the clinician may determine one or more therapy programs that may provide efficacious therapy to patient 112 to address symptoms associated with the patient condition, and, in some cases, specific to one or more different patient states, such as a sleep state, movement state or rest state. For example, the clinician may select one or more stimulation electrode combinations with which stimulation is delivered to brain 120. During the programming session, the clinician may evaluate the efficacy of the specific program being evaluated based on feedback provided by patient 112 or based on one or more physiological parameters of patient 112 (e.g., muscle activity, muscle tone, rigidity, tremor, etc.). Alternatively, identified patient behavior from video information may be used as feedback during the initial and subsequent programming sessions. Programmer 104 may assist the clinician in the creation/identification of therapy programs by providing a methodical system for identifying potentially beneficial therapy parameter values.

However, as described in this disclosure, in some examples, IMD 106 or programmer 104 (e.g., a medical device), alone or in combination, may automatically determine electrode configuration and therapy parameters. For example, the medical device may determine which electrodes to use for stimulation based on which electrodes are most proximal to the LFP source. As described in more detail, the medical device may also titrate the amplitude or another parameter of the stimulation to automatically determine the stimulation amplitude. In some examples, programmer 104 may output information indicating the selected electrode configuration for stimulation and the determined stimulation amplitude or other therapy parameter for the clinician or physician to review and confirm before IMD 106 delivers therapy via the selected electrode configuration with the determined stimulation amplitude.

Programmer 104 may also be configured for use by patient 112. When configured as a patient programmer, programmer 104 may have limited functionality (compared to a clinician programmer) in order to prevent patient 112 from altering critical functions of IMD 106 or applications that may be detrimental to patient 112. In this manner, programmer 104 may only allow patient 112 to adjust values for certain therapy parameters or set an available range of values for a particular therapy parameter.

Programmer 104 may also provide an indication to patient 112 when therapy is being delivered, when patient input has triggered a change in therapy or when the power source within programmer 104 or IMD 106 needs to be replaced or recharged. For example, programmer 104 may include an alert LED, may flash a message to patient 112 via a programmer display, generate an audible sound or somatosensory cue to confirm patient input was received, e.g., to indicate a patient state or to manually modify a therapy parameter.

Therapy system 100 may be implemented to provide chronic stimulation therapy to patient 112 over the course of several months or years. However, system 100 may also be employed on a trial basis to evaluate therapy before committing to full implantation. If implemented temporarily, some components of system 100 may not be implanted within patient 112. For example, patient 112 may be fitted with an external medical device, such as a trial stimulator, rather than IMD 106. The external medical device may be coupled to percutaneous leads or to implanted leads via a percutaneous extension. If the trial stimulator indicates DBS system 100 provides effective treatment to patient 112, the clinician may implant a chronic stimulator within patient 112 for relatively long-term treatment.

Although IMD 106 is described as delivering electrical stimulation therapy to brain 120, IMD 106 may be configured to direct electrical stimulation to other anatomical regions of patient 112. Further, an IMD may provide other electrical stimulation such as spinal cord stimulation to treat a movement disorder.

According to the techniques of the disclosure, a medical device (e.g., IMD 106 or programmer 104) of system 100 may be configured to determine therapy parameters for electrical stimulation delivered via electrodes 116, 118. To determine the therapy parameters, the medical device may first determine orientation of the LFP source. One example of the orientation of the LFP source is a determination of which ones of electrodes 116, 118 are most proximal to the LFP source. One example of the orientation of the LFP source is a determination of the distance and/or location of the LFP source relative to electrodes 116, 118 or a location of the LFP source within brain 120 inferred based on the electrodes having the highest CSD, as described in more detail below.

There are various example techniques for determining orientation of the LFP source. As one example, IMD 106 may receive multiple recordings of the bioelectric signal generated by the LFP source via electrodes 116, 118. The multiple recordings of the bioelectric signals may be multiple voltage measurements of the bioelectric signal. IMD 106 may band pass filter the multiple recordings of the bioelectric signal to generate a plurality of filtered signals, where each filtered signal is from each of electrodes 116, 118. For instance, IMD 106 may generate a first filtered signal from the output of a first one of electrodes 116 that sensed the bioelectric signal generated by the LFP source, generate a second filtered signal for a second one of electrodes 116, and so forth.

From each of the filtered signals, IMD 106 may determine a current source density (CSD) value for each respective electrodes 116, 118. For example, the CSD values may be computed using all the signals from all the electrodes 116, 118. A single CSD value for a given electrode may need the signals sensed by that electrode and from adjacent electrodes. The CSD value of an electrode is a measure of the net current flow across an electrode. IMD 106 may determine which ones of electrodes 116, 118 have the highest CSD value. The electrodes 116, 118 having the highest CSD values tend to be electrodes most proximal to the LFP source, and also tend to be the electrodes (or neighbor electrodes) that should be used to deliver the electrical stimulation therapy. Hence, the CSD value may be used to infer proximity of an electrode to an LFP source.

One example way to determine the CSD for respective electrodes is based on voltage differences of adjacent electrodes. For example, IMD 106 may determine CSD values based on the voltage differences between the adjacent electrodes. In some examples, the CSD values may be the second spatial difference of voltage difference along the electrodes. Each of the second spatial difference of voltage differences may be a difference between the voltage differences. In other words, in some examples, the CSD values may be the differences between the voltage differences along the lead. In a more specific example, the two CSD values for a four-electrode system would be $(V_1-V_2)-(V_2-V_3)$ and $(V_2-V_3)-(V_3-V_4)$.

IMD 106 may determine a CSD value for each electrode that is between two other electrodes. In general, in systems that include N electrodes, IMD 106 may determine N−2 CSD values, each of which may be associated with a different one of the electrodes. The end electrodes (e.g., the electrodes not arranged between two adjacent electrodes) may not have associated CSD values in some examples because the outside electrodes may not be associated with two different voltage difference values.

There may be other ways in which to determine the orientation or direction of the LFP source (e.g., based on proximity of electrodes), and the example techniques to determine the orientation of the LFP source should not be considered limiting. There may also be other ways in which to determine the CSD values, and the example techniques to determine the CSD values should not be considered limiting. Example techniques to determine the orientation of the LFP source are described in U.S. Patent Publication No. 2017/0259064 and U.S. Patent Publication No. 2014/0074187, the contents of which are incorporated herein by reference.

Once the electrodes that should be used to deliver the electrical stimulation are selected, the clinician or patient may need to expend time with a trial-and-error scheme to determine the therapy parameters. Furthermore, there may be times when adjustments to the therapy parameters are not providing any further benefit to the patient, but the clinician may not be able to determine that further adjustment would not benefit the patient.

As one example, in response to delivery of a present electrical stimulation (e.g., using electrodes 116, 118 selected based on the CSD values) having a present therapy parameter value, IMD 106 may determine a present power value of power in a frequency band (e.g., beta band) in the bioelectric signal generated by the LFP source and sensed by sense electrodes. Also assume that IMD 106 had determined, prior to determining the present power, a previous power value of power in the frequency band in response to delivery of a previous electrical stimulation having a previous therapy value different than the present therapy parameter value. In some cases, if the difference between the present power value and the previous power value is less than a threshold value (e.g., 0.5 $uV/\sqrt{Hz}$ as one non-limiting example), further adjustment of the therapy value may not provide noticeably more effective therapy. In other words, there may not be any further benefit of adjusting the therapy value if the delta (e.g., difference) between the present power value and the previous power value is less than the threshold value.

However, the clinician or patient may not be able to determine the power values, much less whether the difference in the present and previous power values is less than or greater than a threshold. Accordingly, the clinician may keep adjusting therapy values until the patient feels side effects even though it was feasible to stop adjusting therapy values earlier.

This disclosure describes example techniques to automate the determination of the therapy values based on a difference between the present power value of the power in the frequency band (e.g., beta band) of a present bioelectric signal and the previous power value of the power in the frequency band of a previous bioelectric signal. For instance, if the difference is greater than a threshold value, the medical device may iteratively adjust the present therapy parameter value and deliver electrical stimulation with the adjusted parameter value until the difference between the present power value (e.g., power value of the power in the frequency band in the current iteration) and the previous power value (e.g., power value of the power in the frequency band in the previous iteration) is less than the threshold value. Once the difference becomes less than the threshold value, the medical device may cease adjustment of the present therapy parameter value and set a final therapy parameter value equal to the present therapy parameter value. The medical device may cause delivery of electrical stimulation having the final therapy parameter value.

For instance, as described above, brain 120 includes an LFP source that generates a bioelectric signal. The power of the bioelectric signal in a frequency band (e.g., beta band) may be based on a therapy parameter value of a therapy parameter in electrical stimulation delivered by IMD 106 via electrodes 116, 118. For instance, for a certain therapy parameter value, the electrical stimulation may suppress the beta band of the bioelectric signal (e.g., such that the power of the beta band is relatively low), which tends to result in a reduction in symptoms for certain conditions such as Parkinson's disease. The present power level is indicative of the present power of the frequency band of the bioelectric signal responsive to the present electrical stimulation, and the previous power level is indicative of the previous power of the frequency band of the bioelectric signal responsive to a previous electrical stimulation. A reduction in the difference between the present power level and the previous power level may be indicative of suppression of the beta band, and when there is no further change between the present power level and the previous power level (e.g., the difference is less than threshold value), then further adjustment of the therapy parameter may not result in any further suppression of the beta band in the bioelectric signal.

In this way, the example techniques may automatically titrate the therapy parameter value based on whether the difference in the present and previous power values is greater than a threshold value. The medical device may more quickly determine the therapy parameter value with limited to no clinician or patient involvement, as compared to a manual trial-and-error process. Moreover, the medical device may cease adjustment of the therapy parameter value when the difference in the present and previous power values is less than the threshold value, which may reduce the amount of therapy parameter values that need to be tested to determine the final therapy parameter value.

Figure 2:
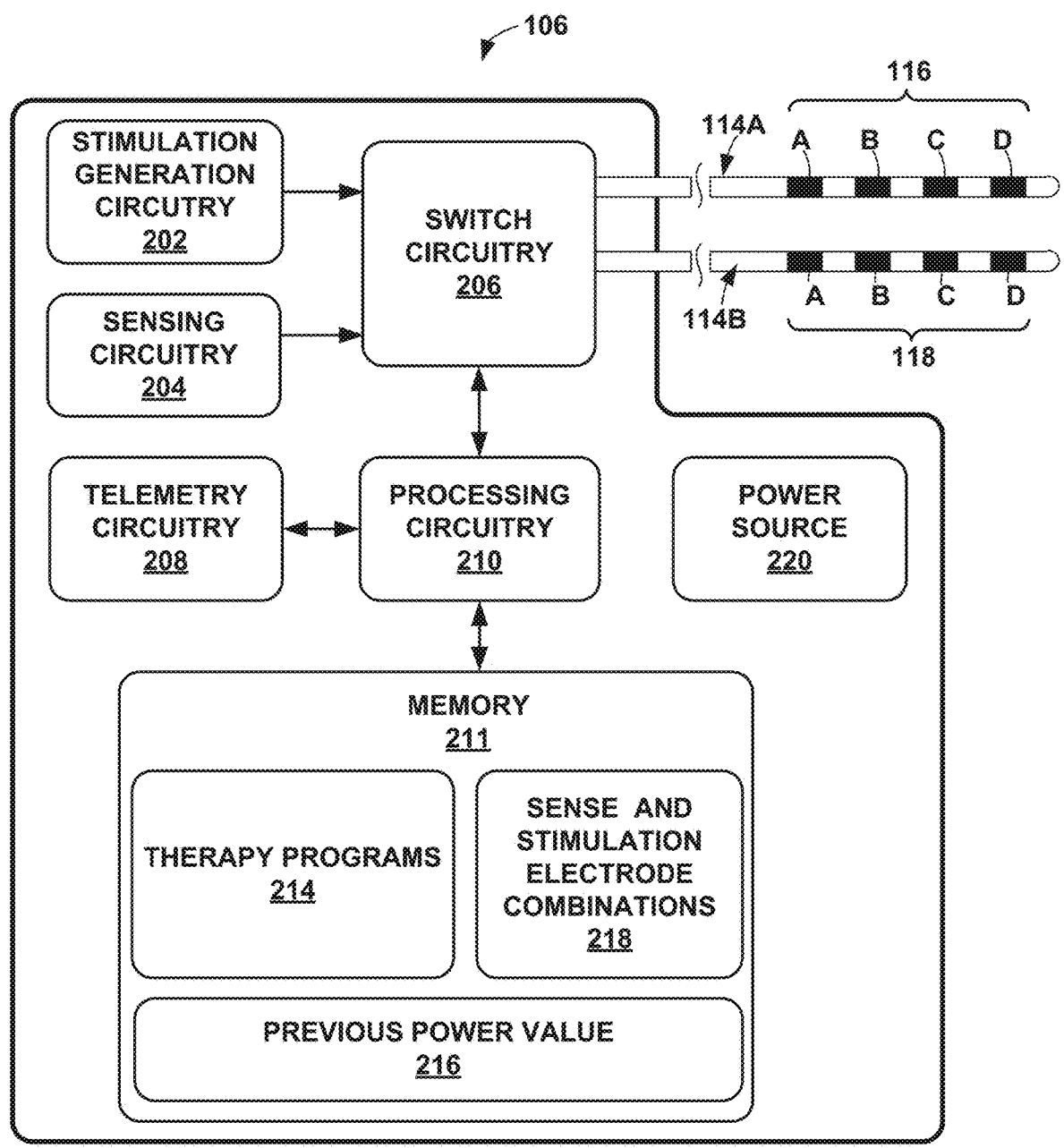
FIG. 2 is a block diagram of the example IMD of FIG. 1 for delivering adaptive DBS therapy according to an example of the techniques of the disclosure.

FIG. 2 is a block diagram of the example IMD 106 of FIG. 1 for delivering adaptive deep brain stimulation therapy. In the example shown in FIG. 2, IMD 106 includes processing circuitry 210, memory 211, stimulation generation circuitry 202, sensing circuitry 204, switch circuitry 206, telemetry circuitry 208, and power source 220. Each of these circuits may be or include electrical circuitry configured to perform the functions attributed to each respective circuit. Memory 211 may include any volatile or non-volatile media, such as a random-access memory (RAM), read only memory (ROM), non-volatile RAM (NVRAM), electrically erasable programmable ROM (EEPROM), flash memory, and the like. Memory 211 may store computer-readable instructions that, when executed by processing circuitry 210, cause IMD 106 to perform various functions. Memory 211 may be a storage device or other non-transitory medium.

In the example shown in FIG. 2, memory 211 stores therapy programs 214, previous power value 216, and sense electrode combinations and associated stimulation electrode combinations 218, in separate memories within memory 211 or separate areas within memory 211. Each stored therapy program 214 defines a particular set of electrical stimulation parameters (e.g., a therapy parameter set), such as a stimulation electrode combination, electrode polarity, current or voltage amplitude, pulse width, and pulse rate. In some examples, individual therapy programs may be stored as a therapy group, which defines a set of therapy programs with which stimulation may be generated. The stimulation signals defined by the therapy programs of the therapy group may be delivered together on an overlapping or non-overlapping (e.g., time-interleaved) basis.

Previous power value 216 is indicative of a power level of power in a frequency band of a bioelectric signal generated in response to delivery of a previous electrical stimulation having a previous therapy parameter value different than the present therapy parameter value. As described in more detail, in some examples, IMD 106 may determine a difference between previous power value 216 and the present power value to determine whether further adjustment to a therapy parameter value is needed as a way to automatically titrate to the therapy parameter to an appropriate value.

Sense and stimulation electrode combinations 218 stores sense electrode combinations and associated stimulation electrode combinations. As described above, in some examples, sense and stimulation electrode combinations 218 may include the same subset of electrodes 116, 118, a housing of IMD 106 functioning as an electrode, or may include different subsets or combinations of such electrodes. Thus, memory 211 can store a plurality of sense electrode combinations and, for each sense electrode combination, store information identifying the stimulation electrode combination that is associated with the respective sense electrode combination. The associations between sense and stimulation electrode combinations can be determined, e.g., by a clinician or automatically by processing circuitry 210. In some examples, corresponding sense and stimulation electrode combinations may comprise some or all of the same electrodes. In other examples, however, some or all of the electrodes in corresponding sense and stimulation electrode combinations may be different. For example, a stimulation electrode combination may include more electrodes than the corresponding sense electrode combination in order to increase the efficacy of the stimulation therapy.

Stimulation generation circuitry 202, under the control of processing circuitry 210, generates stimulation signals for delivery to patient 112 via selected combinations of electrodes 116, 118. An example range of electrical stimulation parameters believed to be effective in DBS to manage a movement disorder of patient include:

1. Pulse Rate, i.e., Frequency: between approximately 40 Hertz and approximately 500 Hertz, such as between approximately 90 to 170 Hertz or such as approximately 90 Hertz.
2. In the case of a voltage controlled system, Voltage Amplitude: between approximately 0.1 volts and approximately 50 volts, such as between approximately 2 volts and approximately 3 volts.
3. In the case of a current controlled system, Current Amplitude: between approximately 1 milliamps to approximately 3.5 milliamps, such as between approximately 1.0 milliamps and approximately 1.75 milliamps.
4. Pulse Width: between approximately 50 microseconds and approximately 500 microseconds, such as between approximately 50 microseconds and approximately 200 microseconds.

Accordingly, in some examples, stimulation generation circuitry 202 generates electrical stimulation signals in accordance with the electrical stimulation parameters noted above. Other ranges of therapy parameter values may also be useful, and may depend on the target stimulation site within patient 112. While stimulation pulses are described, stimulation signals may be of any form, such as continuous-time signals (e.g., sine waves) or the like.

Processing circuitry 210 may include fixed function processing circuitry and/or programmable processing circuitry, and may comprise, for example, any one or more of a microprocessor, a controller, a digital signal processor (DSP), an application specific integrated circuit (ASIC), a field-programmable gate array (FPGA), discrete logic circuitry, or any other processing circuitry configured to provide the functions attributed to processing circuitry 210 herein may be embodied as firmware, hardware, software or any combination thereof. Processing circuitry 210 may control stimulation generation circuitry 202 according to therapy programs 214 stored in memory 211 to apply particular stimulation parameter values specified by one or more of programs, such as voltage amplitude or current amplitude, pulse width, and/or pulse rate.

In the example shown in FIG. 2, the set of electrodes 116 includes electrodes 116A, 116B, 116C, and 116D, and the set of electrodes 118 includes electrodes 118A, 118B, 118C, and 118D. Processing circuitry 210 also controls switch circuitry 206 to apply the stimulation signals generated by stimulation generation circuitry 202 to selected combinations of electrodes 116, 118. In particular, switch circuitry 204 may couple stimulation signals to selected conductors within leads 114, which, in turn, deliver the stimulation signals across selected electrodes 116, 118. Switch circuitry 206 may be a switch array, switch matrix, multiplexer, or any other type of switching module configured to selectively couple stimulation energy to selected electrodes 116, 118 and to selectively sense neurological brain signals with selected electrodes 116, 118. Hence, stimulation generation circuitry 202 is coupled to electrodes 116, 118 via switch circuitry 206 and conductors within leads 114. In some examples, however, IMD 106 does not include switch circuitry 206.

Stimulation generation circuitry 202 may be a single channel or multi-channel stimulation generator. In particular, stimulation generation circuitry 202 may be capable of delivering a single stimulation pulse, multiple stimulation pulses, or a continuous signal at a given time via a single electrode combination or multiple stimulation pulses at a given time via multiple electrode combinations. In some examples, however, stimulation generation circuitry 202 and switch circuitry 206 may be configured to deliver multiple channels on a time-interleaved basis. For example, switch circuitry 206 may serve to time divide the output of stimulation generation circuitry 202 across different electrode combinations at different times to deliver multiple programs or channels of stimulation energy to patient 112. Alternatively, stimulation generation circuitry 202 may comprise multiple voltage or current sources and sinks that are coupled to respective electrodes to drive the electrodes as cathodes or anodes. In this example, IMD 106 may not require the functionality of switch circuitry 206 for time-interleaved multiplexing of stimulation via different electrodes.

Electrodes 116, 118 on respective leads 114 may be constructed of a variety of different designs. For example, one or both of leads 114 may include two or more electrodes at each longitudinal location along the length of the lead, such as multiple electrodes, e.g., arranged as segments, at different perimeter locations around the perimeter of the lead at each of the locations A, B, C, and D. FIGS. 4A-4C illustrate such example leads.

As an example, one or both of leads 114 may include radially-segmented DBS arrays (rDBSA) of electrodes. In the rDBSA, as one example, there may be a first ring electrode of electrodes 116 around the perimeter of lead 114A at a first longitudinal location on lead 114A (e.g., location A). Below the first ring electrode, there may be three segmented electrodes of electrodes 116 around the perimeter of lead 114A at a second longitudinal location on lead 114A (e.g., location B). Below the three segmented electrodes, there may be another set of three segmented electrodes of electrodes 116 around the perimeter of lead 114A at a third longitudinal location of lead 114A (e.g., location C). Below the three segmented electrodes, there may be a second ring electrode of electrodes 116 around the perimeter of lead 114A (e.g., location D). Electrodes 118 may be similarly positioned along lead 114B.

The above is one example of the rDBSA array of electrodes, and the example techniques should not be considered limited to such an example. There may be other configurations of electrodes for DBS. Moreover, the example techniques are not limited to DBS, and other electrode configurations are possible.

In one example, the electrodes 116, 118 may be electrically coupled to switch circuitry 206 via respective wires that are straight or coiled within the housing of the lead and run to a connector at the proximal end of the lead. In another example, each of the electrodes 116, 118 of the leads 114 may be electrodes deposited on a thin film. The thin film may include an electrically conductive trace for each electrode that runs the length of the thin film to a proximal end connector. The thin film may then be wrapped (e.g., a helical wrap) around an internal member to form the leads 114. These and other constructions may be used to create a lead with a complex electrode geometry.

Although sensing circuitry 204 is incorporated into a common housing with stimulation generation circuitry 202 and processing circuitry 210 in FIG. 2, in other examples, sensing circuitry 204 may be in a separate housing from IMD 106 and may communicate with processing circuitry 210 via wired or wireless communication techniques. Example neurological brain signals include, but are not limited to, a signal generated from local field potentials (LFPs) within one or more regions of brain 28. EEG and ECoG signals are examples of local field potentials that may be measured within brain 120. LFPs, EEG and ECoG may be different measurements of the same bioelectric signals in the brain. The neurons generate the signals, and if measured at depth, it is LFP, if measured on the dura, it is ECoG, if on the scalp, it is EEG.

Telemetry circuitry 208 supports wireless communication between IMD 106 and an external programmer 104 or another computing device under the control of processing circuitry 210. Processing circuitry 210 of IMD 106 may receive, as updates to programs, values for various stimulation parameters such as magnitude and electrode combination, from programmer 104 via telemetry circuitry 208. The updates to the therapy programs may be stored within therapy programs 214 portion of memory 211. Telemetry circuitry 208 in IMD 106, as well as telemetry modules in other devices and systems described herein, such as programmer 104, may accomplish communication by radiofrequency (RF) communication techniques. In addition, telemetry circuitry 208 may communicate with external medical device programmer 104 via proximal inductive interaction of IMD 106 with programmer 104. Accordingly, telemetry circuitry 208 may send information to external programmer 104 on a continuous basis, at periodic intervals, or upon request from IMD 106 or programmer 104.

Power source 220 delivers operating power to various components of IMD 106. Power source 220 may include a small rechargeable or non-rechargeable battery and a power generation circuit to produce the operating power. Recharging may be accomplished through proximal inductive interaction between an external charger and an inductive charging coil within IMD 104. In some examples, power requirements may be small enough to allow IMD 104 to utilize patient motion and implement a kinetic energy-scavenging device to trickle charge a rechargeable battery. In other examples, traditional batteries may be used for a limited period of time.

In one example, processing circuitry 210 of IMD 106 senses, via electrodes 116, 118 interposed along leads 114 (and sensing circuitry 204), one or more bioelectric signals of brain 120 of patient 112. Further, processing circuitry 210 of IMD 106 delivers, via electrodes 116, 118 (and stimulation generation circuitry 202), electrical stimulation therapy to patient 112 based on the sensed one or more bioelectric signals of brain 120. The adaptive DBS therapy is defined by one or more therapy programs 214 having one or more parameters stored within memory 211. For example, the one or more parameters include a current amplitude (for a current-controlled system) or a voltage amplitude (for a voltage-controlled system), a pulse rate or frequency, and a pulse width, or a number of pulses per cycle. In examples where the electrical stimulation is delivered according to a "burst" of pulses, or a series of electrical pulses defined by an "on-time" and an "off-time," the one or more parameters may further define one or more of a number of pulses per burst, an on-time, and an off-time. Processing circuitry 210, via electrodes 116, 118, delivers to patient 112 adaptive DBS and may adjust one or more parameters defining the electrical stimulation based on corresponding parameters of the sensed one or more bioelectric signals of brain 120.

In some examples, processing circuitry 210 continuously measures the one or more bioelectric signals in real time. In other examples, processing circuitry 210 periodically samples the one or more bioelectric signals according to a predetermined frequency or after a predetermined amount of time. In some examples, processing circuitry 210 periodically samples the signal at a frequency of approximately 150 Hertz.

According to the techniques of the disclosure, processing circuitry 210 may be configured to determine which electrodes 116, 118 should be used to deliver electrical stimulation (e.g., based on orientation of the LFP source), and configured to determine therapy parameter values for the therapy parameters of the electrical stimulation. To determine which electrodes 116, 118 to use for delivering electrical stimulation, processing circuitry 210 may determine which electrodes 116, 118 have the greatest current source density (CSD) value due to sensing of the LFP signal from the LFP source. However, other techniques to determine which electrodes 116, 118 to use to deliver electrical stimulation are possible.

As one example way to determine the CSD value, processing circuitry 210 may cause sensing circuitry 204 to measure the voltage across pairs of electrodes 116, 118, where the voltage across the pairs of electrodes 116, 118 is due to the bioelectrical signal generated by the LFP source. The result of the measured voltages may be a set of differential voltages. Processing circuitry 210 may then determine the difference between differential voltages of the set of differential voltages to determine a CSD value for one or more of electrodes 116, 118 (expect for possibly the top and bottom electrodes). Processing circuitry 210 may compare the CSD values for electrodes 116, 118 to determine which one(s) of electrodes 116, 118 have the greatest CSD values. The electrodes 116, 118 having the greatest CSD values are the electrodes that tend to be closest to the LFP source and should be used to deliver stimulation.

In this way, processing circuitry 210 may determine which electrodes are most proximal to a signal source (e.g., LFP source) generating the bioelectric signal or have a highest CSD value. Processing circuitry 210 may select the determined electrodes that are most proximal to the signal source (e.g., LFP source) for delivering the electrical stimulation. Processing circuitry 210 may cause stimulation generation circuitry 202 and/or switch circuitry 206 to deliver the electrical stimulation with the selected electrodes.

In addition to determining which electrodes to use to deliver the electrical stimulation, in some examples, processing circuitry 210 may be configured to determine therapy parameter values for the therapy parameters of the electrical stimulation. For ease of description, the following is described with respect to determining an amplitude of the electrical stimulation (e.g., voltage amplitude and/or current amplitude). The example techniques may be applicable to other electrical stimulation parameters such as pulse width and frequency.

Processing circuitry 210 may deploy the example adaptive stimulation protocol described in this disclosure on the selected electrodes 116, 118 (selected in the manner described above) to titrate stimulation for suppression of beta power (e.g., to suppress the beta band frequency component in the bioelectric signal). The example protocol that processing circuitry 210 utilizes is referred to as "ping and listen," in which amplitude of the electrical stimulation is gradually incremented based on suppression of the beta band power derived from simultaneous sensing of the voltage generated from the LFP source (e.g., simultaneous LFP recordings).

For instance, as described in more detail, processing circuitry 210 may utilize the voltage measurements from the LFP source in response to an increase in the amplitude of the electrical stimulation to determine whether the delivery of the electrical stimulation was effective in suppression of the beta band power. In some examples, sensing circuitry 204 may output to processing circuitry 210 the differential voltage between two electrodes that neighbor the selected electrodes used for delivery of the electrical stimulation. Accordingly, processing circuitry 210 may receive information of the bioelectric signal sensed from one or more electrodes that neighbor one of the selected electrodes used for delivering the electrical stimulation. Processing circuitry 210 may be configured to determine the power value of the power in the frequency band (e.g., beta band) based on the received information. Example techniques to determine the power value of the power in the frequency band are described in more detail below.

One example reason to determine the power value of the power in the frequency band based on bioelectric signals sensed by the neighboring electrodes (e.g., immediately adjacent electrodes) to the stimulation electrode is that the impedance of the neighboring electrodes and the stimulation electrodes may be approximately the same, which can minimize stimulation artifact in the bioelectric signal. Although the example describes using electrodes that neighbor the stimulation electrodes for sensing the bioelectric signal in response to delivery of electrical stimulation, the example techniques are not so limited. Other electrodes may be used in addition to or instead of the neighboring electrodes for sensing the bioelectric signal in response to delivery of electrical stimulation.

To determine the therapy parameter value of a therapy parameter, processing circuitry 210 may determine whether delivery of the electrical stimulation caused sufficient difference (e.g., less than a threshold value) in the power in the frequency band (e.g., beta band). If the difference was greater than or equal to the threshold, processing circuitry 210 may keep adjusting the therapy parameter. However, if the difference was less than the threshold, processing circuitry 210 may cease adjustment of the therapy parameter.

For example, processing circuitry 210 may determine a present power value of power in a frequency band in a bioelectric signal, generated in brain 120, in response to delivery of present electrical stimulation having a present therapy parameter value. Processing circuitry 210 may determine a power band difference value between the present power value and a previous power value. The previous power value is indicative of power in the frequency band in a previous bioelectric signal, generated in the brain 120, in response to delivery of a previous electrical stimulation having a previous therapy parameter value different than the present therapy parameter value. One example of the previous power value is previous power value 216 stored in memory 211.

Processing circuitry 210 may compare the power band difference value to a threshold value. Based on the power band difference value being greater than or equal to the threshold value, processing circuitry 210 may iteratively adjust the present therapy parameter value until the power band difference value is less than the threshold value. Processing circuitry 210 may then set a final therapy parameter value equal to the present therapy parameter value, and cause delivery of electrical stimulation having the final therapy parameter value (e.g., via stimulation generation circuitry 202 and/or switch circuitry 206).

As an example, assume that a first set of electrodes 116 were selected as the stimulation electrodes (e.g., based on highest CSD value). Also, assume that a second set of electrodes 116 neighbors the first set of electrodes. Processing circuitry 210 may set the therapy parameter value for the amplitude therapy parameter to a first value (which will later be the previous value) and cause stimulation generation circuitry 202 and/or switch circuitry 206 to deliver electrical stimulation where the amplitude is set by the first value via the first set of electrodes. The second set of electrodes sense the bioelectric signal, and sensing circuitry 204 outputs the sensed bioelectric signal to processing circuitry 210. Processing circuitry 210 then determines the power value of the power in the frequency band (e.g., beta band), and stores the determined power value as previous power value 216.

Processing circuitry 210 may then adjust the therapy parameter value (e.g., increase or decrease the therapy parameter value) to a second value (which is now the present value) and cause stimulation generation circuitry 202 and/or switch circuitry 206 to deliver electrical stimulation where the amplitude is set by the second value via the first set of electrodes. The second set of electrodes sense the bioelectric signal, and sensing circuitry 204 outputs the sensed bioelectric signal to processing circuitry 210. Processing circuitry 210 then determines the power value of the power in the frequency band (e.g., beta band), which is the present power value.

Processing circuitry 210 may determine a power band difference value between the present power value and the previous power value 216, and compare the power band difference value to a threshold value (e.g., predefined or preconfigured threshold value stored in memory 211). If the power band difference value is less than the threshold, processing circuitry 210 may set a final therapy parameter value equal to the present therapy parameter value.

However, if the power band difference value is greater than or equal to the threshold, processing circuitry 210 may iteratively adjust the present therapy parameter value until the power band difference value is less than the threshold value. For example, processing circuitry 210 may set the previous power value 216 equal to the present power value. Then, processing circuitry 210 may adjust the value of the present therapy parameter value to a new present therapy parameter value. Stimulation generation circuitry 202 and/or switch circuitry 206 may then deliver electrical stimulation with the amplitude equal to the new present therapy parameter value. Processing circuitry 210 may receive information of the sensed bioelectric signal from the second set of electrodes and may determine whether the difference between the present power value (e.g., with the new present therapy parameter value) and the previous power value 216 is less than or greater than or equal to the threshold value.

Processing circuitry 210 may keep iterating the therapy parameter value until the difference between the present power value and the previous power value is less than the threshold value. In this way, processing circuitry 210 may titrate the therapy parameter value in a "ping and listen" manner (e.g., where ping is the delivery of electrical stimulation and listen is the sensing of the bioelectric signal) until processing circuitry 210 determines a therapy parameter value where the difference in the power in the frequency band (e.g., beta band) in the bioelectric signal did not change more than a threshold value.

In the above examples, processing circuitry 210 is described as determining a power value of power in a frequency band. The following describes example ways in which processing circuitry 210 may determine the power in the frequency band. However, the example techniques should not be considered limited to the example techniques for determining the power value of power in the frequency band.

Stimulation generation circuitry 202 and/or switch circuitry 206 deliver electrical stimulation in t(s) epochs during which the therapy parameter value of a therapy parameter (e.g., amplitude) is held constant beginning with a minimum therapy parameter value. Sensing circuitry 204 may wait and allow the stimulation to stabilize in a first portion (e.g., first half) of the epoch and processing circuitry 210, based on information of the sensed bioelectric signal outputted by sensing circuitry 204, may compute the power value of the power in the frequency band in a second portion (e.g., second half) of the epoch. One example way in which to determine the power value of the power in the frequency band is by computing the average value of the power in a series w(s) moving window with w/2(s) overlap.

For example, processing circuitry 210 may cause stimulation generation circuitry 202 and/or switch circuitry 206 to deliver electrical stimulation having a present therapy parameter value is for a first time period of t-seconds (e.g., t(s) epoch). To determine the present power value of the power in the frequency band, processing circuitry 210 may during the delivery of the present electrical stimulation having the present therapy parameter value for the first time period of t-seconds, determine a series of power level values starting from a first portion of the first time period of t-seconds (e.g., determine power level values in a window of w(s)). The first portion may be subsequent to a start of the first time period (e.g., half-way point of the first time period). Processing circuitry 210 may determine the present power value of the power in the frequency band based on the series of power level values (e.g., average of the power level values in a window of w(s)).

As described above, in one example, there is w/2(s) overlap in the w(s) window. Accordingly, processing circuitry 210 may start determining the series of power values at a half-way point in the delivery of therapy (e.g., which was for t-seconds). Then, even after stopping the delivery of therapy, processing circuitry 210 may keep determining the series of power values so that the amount of time that processing circuitry 210 delivered the series of power level values is equal to a second time period. In some examples, the first time period and the second time period may be the same.

As an example, to assist with understanding and not to be considered limiting, assume that processing circuitry 210 causes stimulation generation circuitry 202 and/or switch circuitry 206 to deliver electrical stimulation for 500 ms (e.g., the t-seconds for the t(s) epoch is 500 ms). During this 500 ms, processing circuitry 210 may keep the amplitude of the electrical stimulation constant. At a first portion in the t-seconds, subsequent to the start of the first time period of 500 ms, processing circuitry 210 may begin determining the series of power level values. As one example, at the half-way point (e.g., after 250 ms), processing circuitry 210 may begin determining the series of power level values.

After another 250 ms, stimulation generation circuitry 202 and/or switch circuitry 206 may have stopped delivering electrical stimulation (e.g., as described above, in this example, the duration of the time period where therapy is delivered is 500 ms). In some examples, processing circuitry 210 may keep determining the series of power level values even after stimulation generation circuitry 202 and/or switch circuitry 206 have stopped delivering electrical stimulation. For instance, processing circuitry 210 may determine the series of power level values for a second time period. In some examples, the second time period may be different than the first time period, where the first time period was the time that stimulation generation circuitry 202 and/or switch circuitry 206 delivered electrical stimulation. In some examples, the second time period may be the same as the first time period, where the first time period was the time that stimulation generation circuitry 202 and/or switch circuitry 206 delivered electrical stimulation.

For example, if the first time period, during which stimulation generation circuitry 202 and/or switch circuitry 206 delivered electrical stimulation, is equal to 500 ms, and processing circuitry 210 began determining the series of power levels starting at half-way point of 250 ms, then in one example processing circuitry 210 may keep determining the series of power level values for 500 ms (e.g., 250 ms after stimulation generation circuitry 202 and/or switch circuitry 206 delivered electrical stimulation and stopped delivering stimulation). In this example, the t(s) epoch is (e.g., first time period) is 500 ms. The w(s) time period (e.g., second time period) is also equal to 500 ms. Also, because processing circuitry 210 started determining the series of power level values starting from the half-way point and extends beyond the time when electrical stimulation is being delivered, there is w/2(s) time overlap with when electrical stimulation was being delivered and when processing circuitry 210 was determining the series of power level values.

In the above example, processing circuitry 210 may stop adjusting the therapy parameter value until the difference in the present and previous power values is less than a threshold value. In some examples, if the patient experiences any side effects during the adjustment of the therapy parameter value, the patient may be able to stop the adjustment of the therapy parameter value. Accordingly, at the end of a stimulation time period, processing circuitry 210 may compute the absolute difference in the present power value and the previous power value and collect any patient feedback for adverse side effects. Based on the absolute difference in the power values (and in some examples based on the patient feedback), processing circuitry 210 may adjust the therapy parameter value until processing circuitry 210 determines the final therapy parameter value used for delivering electrical stimulation.

One example of the protocol that processing circuitry 210 may employ to determine the therapy parameter value is given by the following pseudo code. The variables in the pseudo code are as follows: Amin is the minimum stimulation amplitude but is updated on each iteration, Amax is the maximum stimulation amplitude, A is the present stimulation amplitude (e.g., present therapy parameter value), SE is the side effect state, "threshold value" is the tolerance in the frequency band difference (e.g., beta band), Pcurr is the present power value, and Pprev is the previous power value.

```
while (delta P ≥ threshold value & SE = No)
    A = Amin + ((Amax − Amin)/2);
    stimulate with amplitude A and sense the bioelectric signal (e.g., record LFP);
    collect patient feedback on side effects;
    if (SE = Yes)
        Amax = A;
    else (SE = No)
        Amin = A;
    determine delta P = absolute value(Pcurr − Pprev)
end
```

In the above example, processing circuitry 210 may iteratively set the previous therapy parameter value (e.g., Amin) equal to the present therapy parameter value (e.g., A). For instance, in the above pseudo-code, processing circuitry 210 may set Amin=A. Processing circuitry 210 may also iteratively adjust the present therapy parameter value to a new present therapy parameter value. In the above pseudo-code, to adjust the present therapy parameter value, processing circuitry 210 may set A=Amin+((Amax−Amin)/2). Setting A=Amin+((Amax−Amin)/2), where Amin was the previous therapy parameter value, may be considered as processing circuitry 210 applying a binary search algorithm. However, other types of algorithms (e.g., instead of or in addition to a binary search algorithm) are possible. In the above example, processing circuitry 210 may iteratively set the previous therapy parameter value equal to the present therapy parameter value and adjust the present therapy parameter value until the power difference value falls below the tolerance value (e.g., threshold value) and there are no reports of side effects.

Figure 3:
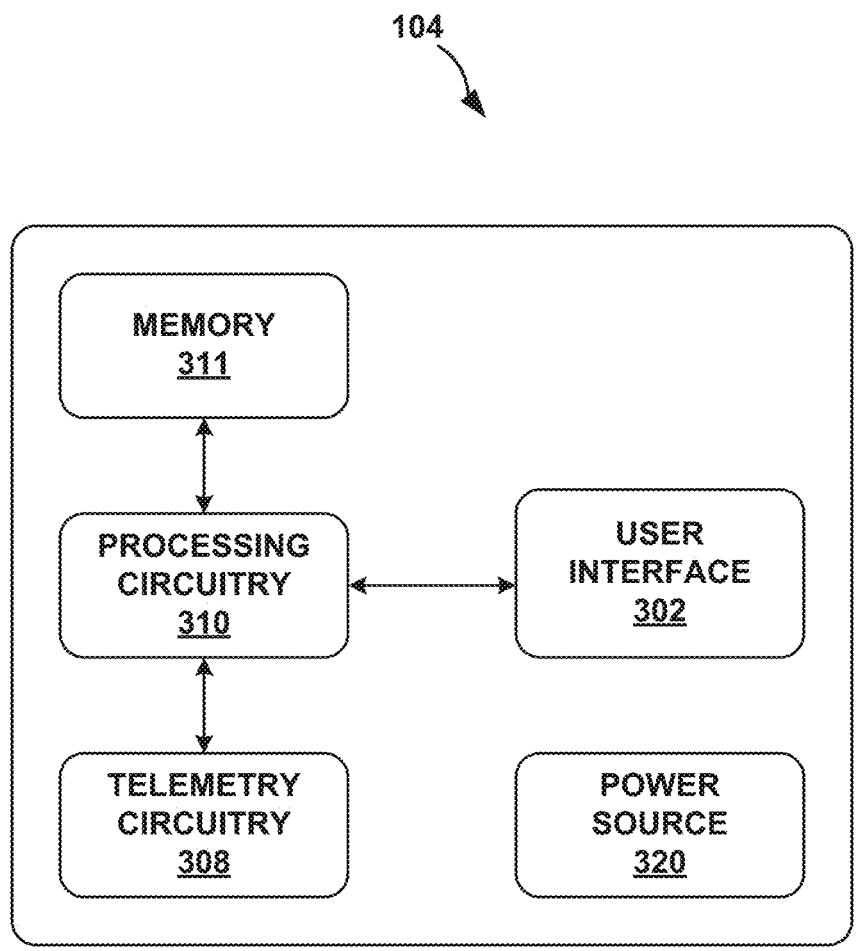
FIG. 3 is a block diagram of the external programmer of FIG. 1 for controlling delivery of adaptive DBS therapy according to an example of the techniques of the disclosure.

FIG. 3 is a block diagram of the external programmer 104 of FIG. 1. Although programmer 104 may generally be described as a hand-held device, programmer 104 may be a larger portable device or a more stationary device. In addition, in other examples, programmer 104 may be included as part of an external charging device or include the functionality of an external charging device. As illustrated in FIG. 3, programmer 104 may include processing circuitry 310, memory 311, user interface 302, telemetry circuitry 308, and power source 320. Memory 311 may store instructions that, when executed by processing circuitry 310, cause processing circuitry 310 and external programmer 104 to provide the functionality ascribed to external programmer 104 throughout this disclosure. Each of these components, or modules, may include electrical circuitry that is configured to perform some or all of the functionality described herein. For example, processing circuitry 310 may include processing circuitry configured to perform the processes discussed with respect to processing circuitry 310.

In general, programmer 104 comprises any suitable arrangement of hardware, alone or in combination with software and/or firmware, to perform the techniques attributed to programmer 104, and processing circuitry 310, user interface 302, and telemetry circuitry 308 of programmer 104. In various examples, programmer 104 may include one or more processors, which may include fixed function processing circuitry and/or programmable processing circuitry, as formed by, for example, one or more microprocessors, DSPs, ASICs, FPGAs, or any other equivalent integrated or discrete logic circuitry, as well as any combinations of such components. Programmer 104 also, in various examples, may include a memory 311, such as RAM, ROM, PROM, EPROM, EEPROM, flash memory, a hard disk, a CD-ROM, comprising executable instructions for causing the one or more processors to perform the actions attributed to them. Moreover, although processing circuitry 310 and telemetry circuitry 308 are described as separate modules, in some examples, processing circuitry 310 and telemetry circuitry 308 may be functionally integrated with one another. In some examples, processing circuitry 310 and telemetry circuitry 308 correspond to individual hardware units, such as ASICs, DSPs, FPGAs, or other hardware units.

Memory 311 (e.g., a storage device) may store instructions that, when executed by processing circuitry 310, cause processing circuitry 310 and programmer 104 to provide the functionality ascribed to programmer 104 throughout this disclosure. For example, memory 311 may include instructions that cause processing circuitry 310 to obtain a parameter set from memory or receive a user input and send a corresponding command to IMD 106, or instructions for any other functionality. In addition, memory 311 may include a plurality of programs, where each program includes a parameter set that defines stimulation therapy.

User interface 302 may include a button or keypad, lights, a speaker for voice commands, a display, such as a liquid crystal (LCD), light-emitting diode (LED), or organic light-emitting diode (OLED). In some examples the display may be a touch screen. User interface 302 may be configured to display any information related to the delivery of stimulation therapy, identified patient behaviors, sensed patient parameter values, patient behavior criteria, or any other such information. User interface 302 may also receive user input via user interface 302. The input may be, for example, in the form of pressing a button on a keypad or selecting an icon from a touch screen.

Telemetry circuitry 308 may support wireless communication between IMD 106 and programmer 104 under the control of processing circuitry 310. Telemetry circuitry 308 may also be configured to communicate with another computing device via wireless communication techniques, or direct communication through a wired connection. In some examples, telemetry circuitry 308 provides wireless communication via an RF or proximal inductive medium. In some examples, telemetry circuitry 308 includes an antenna, which may take on a variety of forms, such as an internal or external antenna.

Examples of local wireless communication techniques that may be employed to facilitate communication between programmer 104 and IMD 106 include RF communication according to the 802.11 or Bluetooth specification sets or other standard or proprietary telemetry protocols. In this manner, other external devices may be capable of communicating with programmer 104 without needing to establish a secure wireless connection.

In some examples, processing circuitry 310 of external programmer 104 defines the parameters of electrical stimulation therapy, stored in memory 311, for delivering adaptive DBS to patient 112. In one example, processing circuitry 310 of external programmer 104, via telemetry circuitry 308, issues commands to IMD 106 causing IMD 106 to deliver electrical stimulation therapy via electrodes 116, 118 via leads 114.

In one or more examples, programmer 104 may be configured to perform one or more of the example techniques described in this disclosure. For instance, processing circuitry 310 may be configured to perform any of the example operations described above with respect to processing circuitry 210. For example, as described above, IMD 106 includes sensing circuitry 204 to receive the bioelectric signals from one or more electrodes, and stimulation generation circuitry 202 to deliver the electrical stimulation having the final therapy parameter value. In some examples, telemetry circuitry 308 may be configured to receive information of the bioelectric signals received by sensing circuitry 204 (e.g., telemetry circuitry 208 of IMD 106 may output information of the bioelectric signal to telemetry circuitry 308 of programmer 104). Processing circuitry 310 may perform the example operations described above with respect to processing circuitry 210 and determine a final therapy parameter value. Processing circuitry 310 may then cause telemetry circuitry 308 to output the final therapy parameter value to IMD 106 to cause delivery of the electrical stimulation having the final therapy parameter value.

FIGS. 4A-4C are conceptual diagrams illustrating an example operation for determining therapy parameter values in accordance with an example of the techniques of this disclosure. FIGS. 4A-4C illustrate one example of lead 114A as one example to assist with understanding. The electrodes on FIGS. 4A-4C illustrate example configuration for rDBSA electrodes.

FIG. 4A illustrates examples of the waveforms of bioelectric signals recorded by electrodes 116 of lead 114A. The waves on the left and the waves on the right of lead 114A illustrate the incoming LFP signals. FIG. 4B illustrates an example of LFP source 402 that may be generating the bioelectric signals sensed by electrodes 116. Based on the sensed bioelectric signals, processing circuitry 210 or 310 may determine which electrodes are most proximal to the signal source (e.g., LFP source 402) or have a highest CSD value. For instance, assume that processing circuitry 210 or 310 determined that electrodes 116A and 116B had the highest CSD values, and are therefore considered to be most proximal to LFP source 402. The circular rings around LFP source 402 are used to illustrate that LFP source 402 may an oscillatory signal source.

In this example, stimulation generation circuitry 202 and/or switch circuitry 206 may utilize electrodes 116A and 116B to deliver the electrical stimulation. As one example, stimulation generation circuitry 202 and/or switch circuitry 206 may output electrical stimulation via selected segments of the electrodes 116A and 116B based on which ones of electrodes of electrodes 116A and 116B are most proximal to the LFP source 402 allowing for directional stimulation.

For instance, FIG. 4C illustrates an example of iteratively adjusting the therapy parameter value for the amplitude (e.g., illustrated by the growing size of the electric bolt) to stimulate a volume of neural tissue (illustrated by the dashed lines) to suppress the beta band frequency component of the bioelectric signal generated by LFP source 402. In this way, processing circuitry 210 or 310 may adaptively titrate to the correct therapy parameter value for the amplitude of the electrical stimulation.

Figure 5:
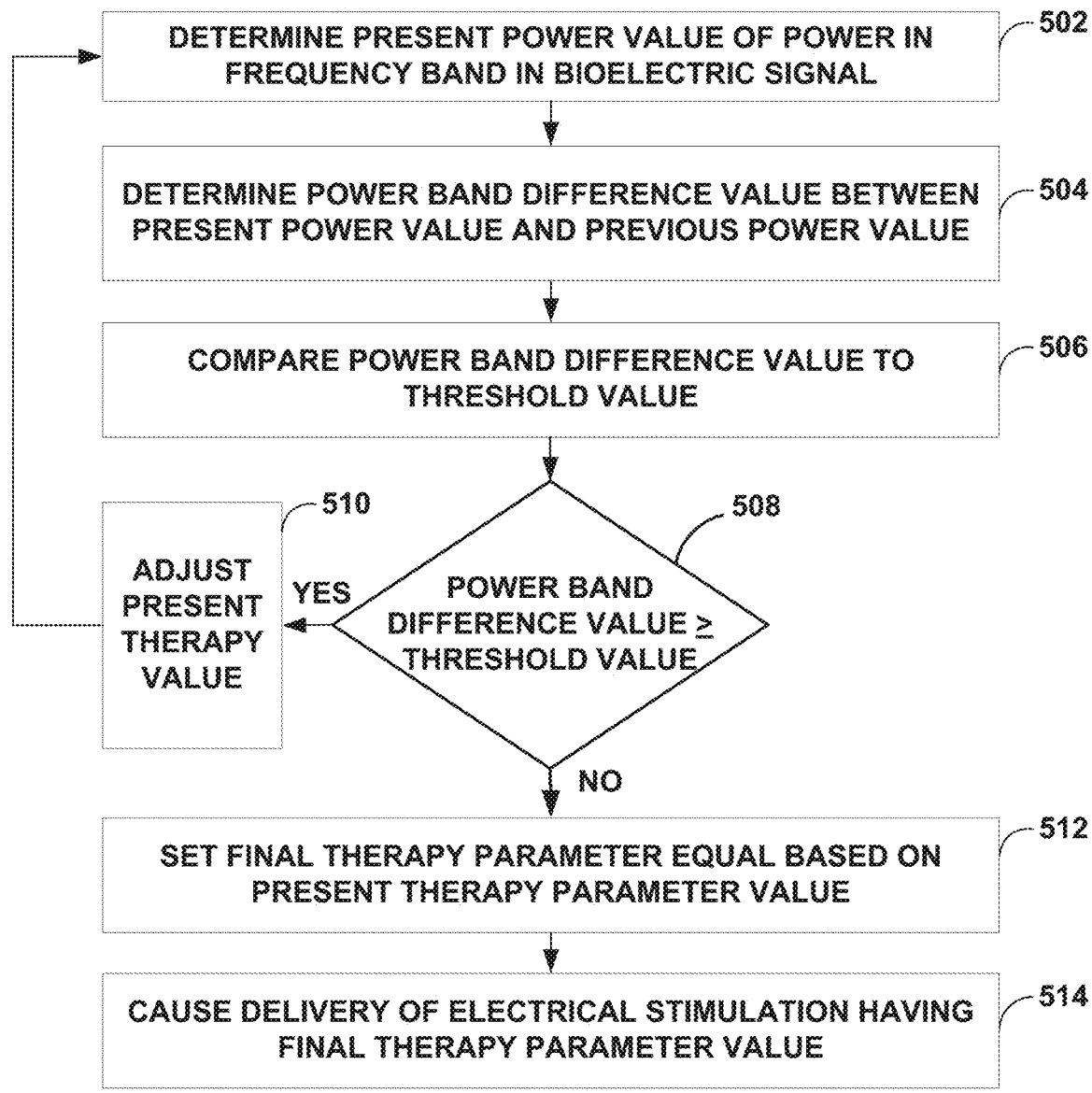
FIG. 5 is a flowchart illustrating an example operation in accordance with techniques of the disclosure.

FIG. 5 is a flowchart illustrating an example operation in accordance with the techniques of the disclosure. For convenience, FIG. 5 is described with respect to FIG. 2, such as where the medical device is IMD 106. However, the example techniques may be performed other examples of medical devices such as programmer 104.

As illustrated, processing circuitry 210 may determine a present power value of power in a frequency band in a bioelectric signal (e.g., beta frequency band from 13 to 33 Hz in the bioelectric signal), generated in brain 120, in response to delivery of present electrical stimulation having a present therapy parameter value (502). As one example, processing circuitry 210 may determine which electrodes are most proximal to a signal source (e.g., LFP source) generating the bioelectric signal or have a highest current source density (CSD) value. The electrodes used for stimulation may be the same as the electrodes that sensed the bioelectrical signal. Processing circuitry 210 may select the determined electrodes that are most proximal to the signal source for delivering the electrical stimulation. To determine the present power value of the power in the frequency band, processing circuitry 210 may receive information of the bioelectric signal sensed from one or more electrodes that neighbor (e.g., same axial level or different axial levels) one of the selected electrodes and determine the present power value of the power in the frequency band based on the received information.

There may be various ways in which to determine the power in the frequency band. As one example, processing circuitry 210 may cause stimulation generation circuitry 202 and/or switch circuitry 206 to deliver the present electrical stimulation having the present therapy parameter value for a first time period of t-seconds. During the delivery of the present electrical stimulation having the present therapy parameter value for the first time period of t-seconds, processing circuitry 210 may determine a series of power level values starting from a first portion of the first time period of t-seconds. The first portion is subsequent to a start of the first time period. As one example, processing circuitry 210 may determine the series of power level values starting from a half-way point in the first time period.

Processing circuitry 210 may determine the present power value of the power in the frequency band based on the series of power level values (e.g., such as based on an average of the power level values). For example, processing circuitry 210 may determine the series of power level values for a second time period. In some examples, the second time period is equal to the t-seconds of the first time period.

Processing circuitry 210 may determine a power band difference value between the present power value and a previous power value (504). The previous power value may be indicative of power in the frequency band in a previous bioelectric signal, generated in brain 120, in response to delivery of a previous electrical stimulation having a previous therapy parameter value different than the present therapy parameter value. For example, prior to delivery of the electrical stimulation having the present therapy parameter value, IMD 106 may have delivered a previous electrical stimulation having a previous therapy parameter and determined the power in the frequency band in the previous bioelectric signal. Processing circuitry 210 may store the previous power value in memory 211 as previous power value 216.

In one example, to determine the power band difference, processing circuitry 210 may subtract the previous power value 216 from the present power value and determine the absolute value of the result. However, the example techniques are not so limited.

Processing circuitry 210 may compare the power band difference value to a threshold value (506). The threshold value may be a tolerance value, where if the power band difference value is less than the threshold value, any further adjustment of the present therapy parameter value may not be felt by patient 112 and any further adjustment of the therapy parameter value may result in little to no increase in the efficacy of the therapy. However, if the power band difference value is greater than or equal to the threshold value, the further adjustment of the present therapy parameter value may be needed.

Accordingly, processing circuitry 210 may determine whether power band difference value is greater than or equal to the threshold value (508). Based on the power band difference value being greater than or equal to the threshold value (YES of 508), processing circuitry 210 may adjust the present therapy value (510). For example, processing circuitry 210 may set the previous therapy parameter value equal to the present therapy parameter value and adjust the present therapy parameter value based on the previous therapy parameter value and a maximum of the therapy parameter value. One such example is using the binary search algorithm, where A=Amin+((Amax−Amin)/2). In this example, A represents the new present therapy parameter value (e.g., the result of adjusting the present therapy parameter value), Amin represents the previous therapy parameter value (which was the present therapy parameter value before adjustment), and Amax is the maximum therapy parameter value. Other algorithms in addition to or instead of the binary search algorithm are possible. Processing circuitry 210 may iteratively loop through the example illustrated in FIG. 5 until processing circuitry 210 determines that the power band difference value is less than the threshold value (NO of 508).

In this manner, processing circuitry 210 may iteratively set the previous therapy parameter value equal to the present therapy parameter value and adjust the present therapy parameter value until the power band difference value is less than the threshold value. In some examples, processing circuitry 210 may adjust the present therapy parameter value based on the maximum therapy parameter value, and possibly the previous therapy parameter value (which would be the present therapy parameter value before adjustment).

Based on the power band different value being less than the threshold value (NO of 508), processing circuitry 210 may set a final therapy parameter value based on the present therapy parameter value (512). Processing circuitry 210 then may cause delivery of electrical stimulation having the final therapy parameter value (514).

The techniques described in this disclosure may be implemented, at least in part, in hardware, software, firmware or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in a computer-readable medium, such as a computer-readable storage medium, containing instructions. Instructions embedded or encoded in a computer-readable storage medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

Various examples have been described. These and other examples are within the scope of the following claims.

What is claimed is:

1. A method comprising:
   determining, with processing circuitry, a present power value of power in a frequency band in a bioelectric signal, generated in a brain, in response to delivery of present electrical stimulation having a present therapy parameter value;
   determining, with the processing circuitry, a power band difference value between the present power value and a previous power value, wherein the previous power value is indicative of power in the frequency band in a previous bioelectric signal, generated in the brain, in response to delivery of a previous electrical stimulation having a previous therapy parameter value different than the present therapy parameter value, and wherein the power band difference value is indicative of a difference between the present power value and the previous power value;
   comparing, with the processing circuitry, the power band difference value to a threshold value;
   based on the power band difference value being greater than or equal to the threshold value, iteratively setting, with the processing circuitry, the previous therapy parameter value equal to the present therapy parameter value and adjusting, with the processing circuitry, the present therapy parameter value until the power band difference value is less than the threshold value;
   setting, with the processing circuitry, a final therapy parameter value based on the present therapy parameter value; and
   causing, with the processing circuitry, delivery of electrical stimulation having the final therapy parameter value.

2. The method of claim 1, wherein the frequency band is a beta frequency band from 13 to 33 Hz in the bioelectric signal.

3. The method of claim 1, further comprising:
   determining which electrodes are most proximal to a signal source generating the bioelectric signal or have a highest current source density (CSD) value; and
   selecting the determined electrodes for delivering the electrical stimulation,
   wherein causing delivery of the electrical stimulation comprises causing delivery of the electrical stimulation with the selected electrodes.

4. The method of claim 3, wherein determining the present power value of the power in the frequency band comprises:
   receiving information of the bioelectric signal sensed from one or more electrodes that neighbor one of the selected electrodes; and
   determining the present power value of the power in the frequency band based on the received information.

5. The method of claim 1, wherein the delivery of the present electrical stimulation having the present therapy parameter value is for a first time period of t-seconds, and wherein determining the present power value of the power in the frequency band comprises:
   during the delivery of the present electrical stimulation having the present therapy parameter value for the first time period of t-seconds, determining a series of power level values starting from a first portion of the first time period of t-seconds, wherein the first portion is subsequent to a start of the first time period; and
   determining the present power value of the power in the frequency band based on the series of power level values.

6. The method of claim 5, wherein determining the series of power level values comprises determining the series of the power level values starting from a half-way point in the first time period.

7. The method of claim 5, wherein determining the series of power level values comprises determining the series of power level values for a second time period that is equal to the t-seconds of the first time period.

8. The method of claim 1, wherein adjusting the present therapy parameter value comprises:
   determining a maximum therapy parameter value; and
   iteratively adjusting the present therapy parameter value based on a difference between the present therapy parameter value and the maximum therapy parameter value.

9. A system comprising:
   a medical device comprising:
      a memory; and
      processing circuitry configured to:
         determine a present power value of power in a frequency band in a bioelectric signal, generated in a brain, in response to delivery of present electrical stimulation having a present therapy parameter value;
         determine a power band difference value between the present power value and a previous power value, wherein the previous power value is indicative of the power in the frequency band in a previous bioelectric signal, generated in the brain, in response to delivery of a previous electrical stimulation having a previous therapy parameter value different than the present therapy parameter value, wherein the power band difference value is indicative of a difference between the present power value and the previous power value, and wherein the power value is stored in the memory;

compare the power band difference value to a threshold value;

based on the power band difference value being greater than or equal to the threshold value, iteratively set the previous therapy parameter value equal to the present therapy parameter value and adjust the present therapy parameter value until the power band difference value is less than the threshold value;

set a final therapy parameter value based on the present therapy parameter value; and cause delivery of electrical stimulation having the final therapy parameter value.

10. The system of claim 9, wherein the medical device comprises an implantable medical device (IMD), wherein the IMD comprises:

sensing circuitry configured to receive the bioelectric signal from one or more electrodes; and stimulation circuitry configured to deliver the electrical stimulation having the final therapy parameter value.

11. The system of claim 9, wherein the medical device comprises a programmer, wherein the programmer comprises:

telemetry circuitry configured to receive information, from an implantable medical device (IMD), of the bioelectric signal and the previous bioelectric signal, wherein, to cause delivery of the electrical stimulation, the processing circuitry is configured to cause the telemetry circuitry to output the final therapy parameter value to the IMD.

12. The system of claim 9, wherein the frequency band is a beta frequency band from 13 to 33 Hz in the bioelectric signal.

13. The system of claim 9, wherein the processing circuitry is configured to:

determine which electrodes are most proximal to a signal source generating the bioelectric signal or have a highest current source density (CSD) value; and select the determined electrodes for delivering the electrical stimulation, wherein to cause delivery of the electrical stimulation, the processing circuitry is configured to cause delivery of the electrical stimulation with the selected electrodes.

14. The system of claim 13, wherein to determine the present power value of the power in the frequency band, the processing circuitry is configured to:

receive information of the bioelectric signal sensed from one or more electrodes that neighbor one of the selected electrodes; and determine the present power value of the power in the frequency band based on the received information.

15. The system of claim 9, wherein the delivery of the present electrical stimulation having the present therapy parameter value is for a first time period of t-seconds, and wherein to determine the present power value of the power in the frequency band, the processing circuitry is configured to:

during the delivery of the present electrical stimulation having the present therapy parameter value for the first time period of t-seconds, determine a series of power level values starting from a first portion of the first time period of t-seconds, wherein the first portion is subsequent to a start of the first time period; and determine the present power value of the power in the frequency band based on the series of power level values.

16. The system of claim 15, wherein to determine the series of power level values, the processing circuitry is configured to determine the series of the power level values starting from a half-way point in the first time period.

17. The system of claim 15, wherein to determine the series of power level values, the processing circuitry is configured to determine the series of power level values for a second time period that is equal to the t-seconds of the first time period.

18. The system of claim 9, wherein to adjust the present therapy parameter value, the processing circuitry is configured to:

determine a maximum therapy parameter value; and iteratively adjust the present therapy parameter value based on a difference between the present therapy parameter value and the maximum therapy parameter value.

19. The system of claim 9, wherein the medical device comprises an implantable medical device (1 MB), the system further comprising a programmer configured to be communicatively coupled to the 1 MB.

20. A computer-readable storage medium storing instructions that when executed cause one or more processors of a medical device to:

determine a present power value of power in a frequency band in a bioelectric signal, generated in a brain, in response to delivery of present electrical stimulation having a present therapy parameter value;

determine a power band difference value between the present power value and a previous power value, wherein the previous power value is indicative of power in the frequency band in a previous bioelectric signal, generated in the brain, in response to delivery of a previous electrical stimulation having a previous therapy parameter value different than the present therapy parameter value, and wherein the power band difference value is indicative of a difference between the present power value and the previous power value;

compare the power band difference value to a threshold value;

based on the power band difference value being greater than or equal to the threshold value, iteratively set the previous therapy parameter value equal to the present therapy parameter value and adjust the present therapy parameter value until the power band difference value is less than the threshold value;

set a final therapy parameter value based on the present therapy parameter value; and cause delivery of electrical stimulation having the final therapy parameter value.

21. The computer-readable storage medium of claim 20, wherein the frequency band is a beta frequency band from 13 to 33 Hz in the bioelectric signal.

22. The computer-readable storage medium of claim 20, further comprising instructions that cause the one or processors to:

determine which electrodes are most proximal to a signal source generating the bioelectric signal or have a highest current source density (CSD) value; and select the determined electrodes for delivering the electrical stimulation, wherein the instructions that cause the one or more processors to cause delivery of the electrical stimulation comprise instructions that cause the one or more processors to cause delivery of the electrical stimulation with the selected electrodes.

23. The computer-readable storage medium of claim 22, wherein the instructions that cause the one or more processors to determine the present power value of the power in the frequency band comprise instructions that cause the one or more processors to:
- receive information of the bioelectric signal sensed from one or more electrodes that neighbor one of the selected electrodes; and
- determine the present power value of the power in the frequency band based on the received information.

24. The computer-readable storage medium of claim 20, wherein the delivery of the present electrical stimulation having the present therapy parameter value is for a first time period of t-seconds, and wherein the instructions that cause the one or more processors to determine the present power value of the power in the frequency band comprise instructions that cause the one or more processors to:
- during the delivery of the present electrical stimulation having the present therapy parameter value for the first time period of t-seconds, determine a series of power level values starting from a first portion of the first time period of t-seconds, wherein the first portion is subsequent to a start of the first time period; and
- determine the present power value of the power in the frequency band based on the series of power level values.

* * * * *